(12) United States Patent
Naiki et al.

(10) Patent No.: US 6,954,268 B2
(45) Date of Patent: Oct. 11, 2005

(54) DEFECT INSPECTION APPARATUS

(75) Inventors: Hiroshi Naiki, Ina (JP); Toshihiko Tanaka, Komagane (JP)

(73) Assignee: Olympus Corporation, Tokyo (JP)

(*) Notice: Subject to any disclaimer, the term of this patent is extended or adjusted under 35 U.S.C. 154(b) by 0 days.

(21) Appl. No.: 10/801,402

(22) Filed: Mar. 15, 2004

(65) Prior Publication Data

US 2004/0174518 A1 Sep. 9, 2004

Related U.S. Application Data

(63) Continuation of application No. PCT/JP02/09762, filed on Sep. 24, 2002.

(30) Foreign Application Priority Data

Sep. 21, 2001 (JP) .......................................... 2001-289963
Mar. 22, 2002 (JP) .......................................... 2002-080836

(51) Int. Cl.$^7$ ............................................. G01N 21/88
(52) U.S. Cl. .................................................. 356/237.2
(58) Field of Search ........................... 356/237.2–237.5

(56) References Cited

U.S. PATENT DOCUMENTS

| | | | | |
|---|---|---|---|---|
| 4,875,780 A | * | 10/1989 | Moran et al. ............ | 356/237.2 |
| 5,359,407 A | * | 10/1994 | Suzuki et al. ........... | 356/237.2 |
| 6,559,938 B1 | * | 5/2003 | Smedt .................... | 356/237.5 |
| 6,594,012 B2 | * | 7/2003 | Takeuchi et al. ........ | 356/237.5 |
| 6,606,154 B1 | | 8/2003 | Oda | |
| 6,621,571 B1 | * | 9/2003 | Shishido et al. ........ | 356/237.5 |

FOREIGN PATENT DOCUMENTS

| | | | |
|---|---|---|---|
| JP | 62-42039 | A | 2/1987 |
| JP | 4-304651 | A | 10/1992 |
| JP | 5-64760 | U | 8/1993 |
| JP | 8-125004 | A | 5/1996 |
| JP | 9-61365 | * | 3/1997 |
| JP | 9-061365 | A | 3/1997 |
| JP | 11-051874 | A | 2/1999 |
| JP | 11-219990 | A | 8/1999 |
| JP | 11-219990 | * | 8/1999 |
| JP | 2000-90206 | A | 3/2000 |

* cited by examiner

*Primary Examiner*—Richard A. Rosenberger
(74) *Attorney, Agent, or Firm*—Frishauf, Holtz, Goodman & Chick, P.C.

(57) ABSTRACT

The present invention provides a defect inspection apparatus comprising an inspection section which inspects a front surface and a rear surface of a sample, a control section which processes image data on the front surface and rear surface of the sample obtained by the inspection section, moving section provided in the inspection section and capable of reciprocating the sample, illumination section which illuminates the front surface and rear surface of the sample moved by the moving section, and image pickup section which picks up images of the front surface and rear surface of the sample illuminated by the illumination section, wherein at least one of an incidence angle of the illumination section on the sample and an image pickup angle of the image pickup section to the sample is changeable.

7 Claims, 11 Drawing Sheets

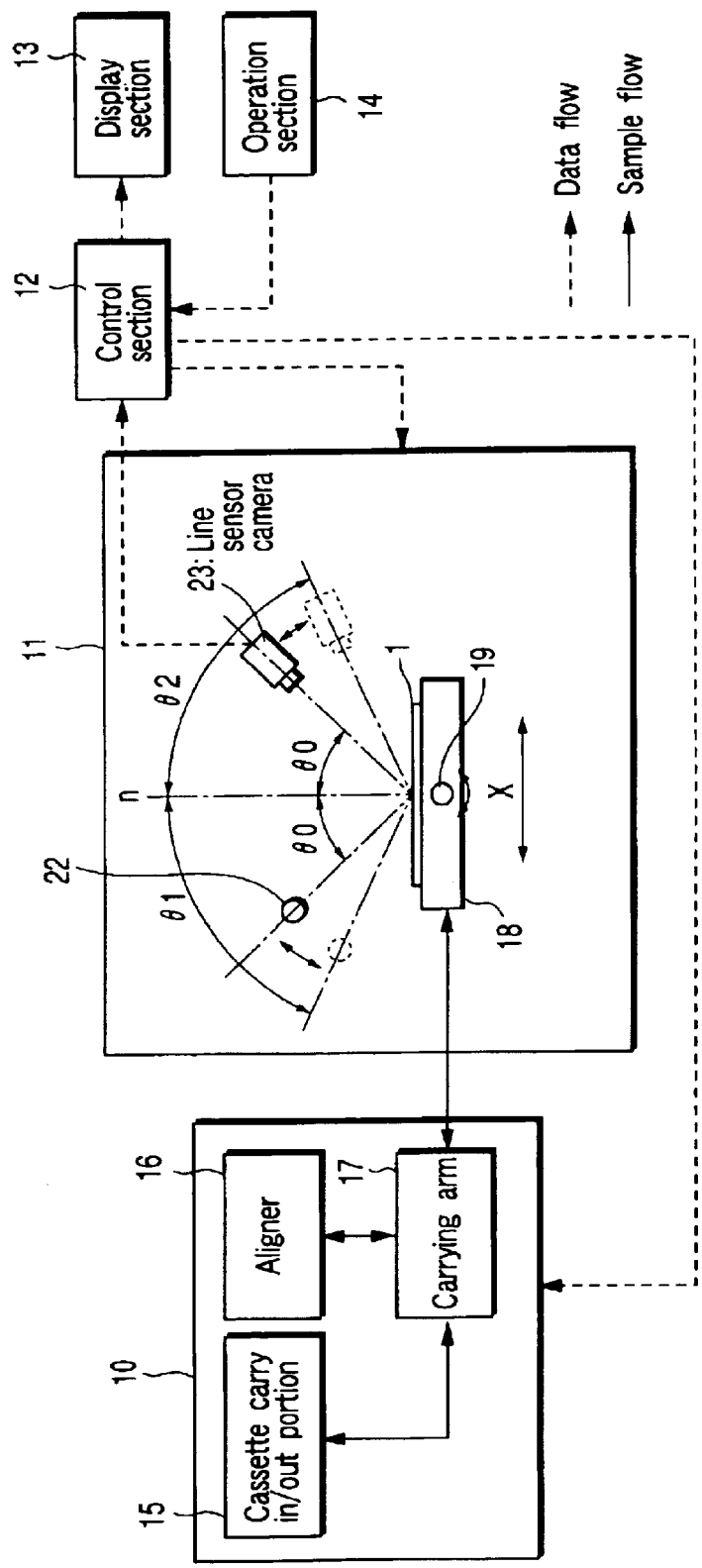
F I G. 1

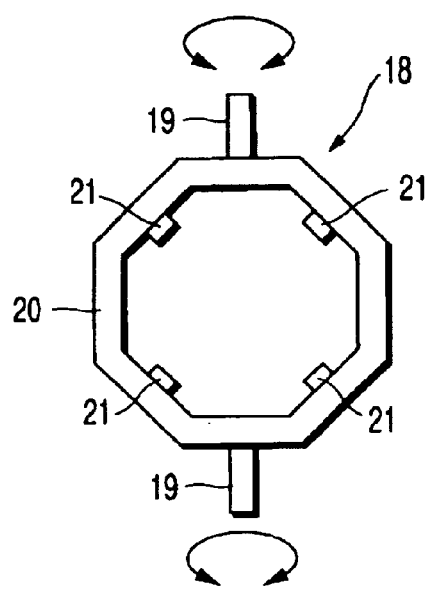
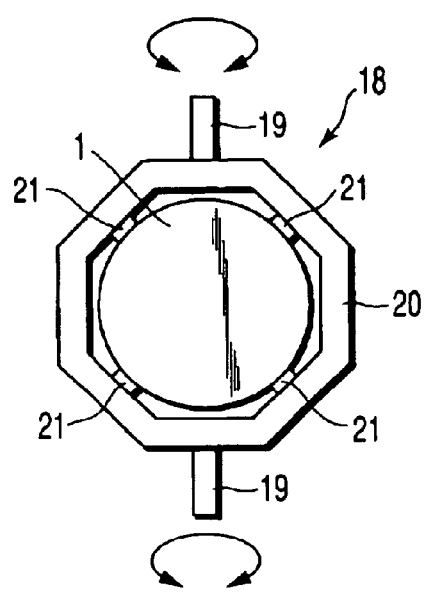
FIG. 2A          FIG. 2B
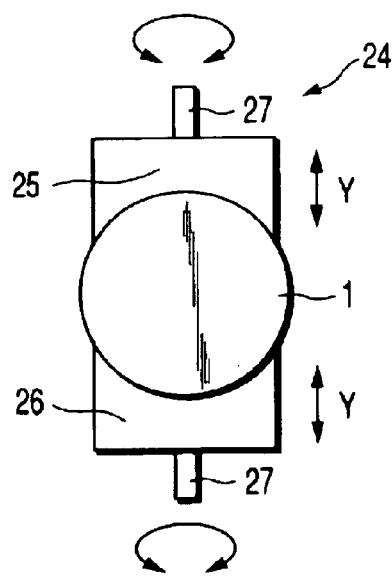
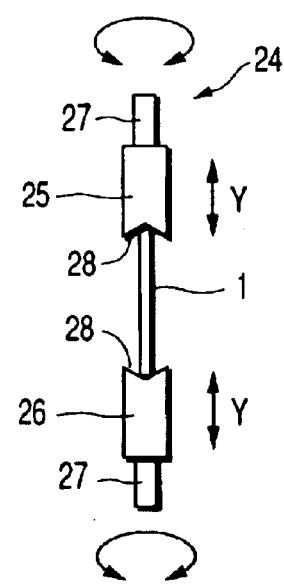
FIG. 3A          FIG. 3B

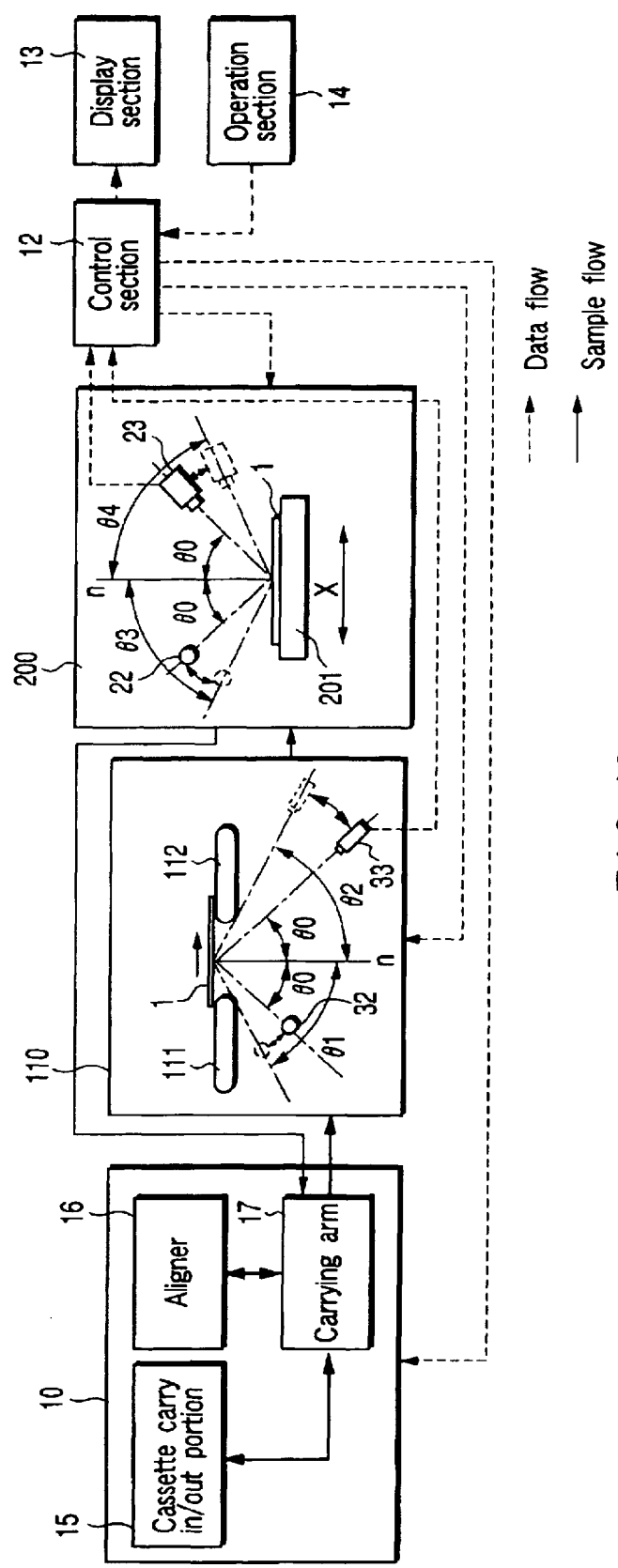
F I G. 12

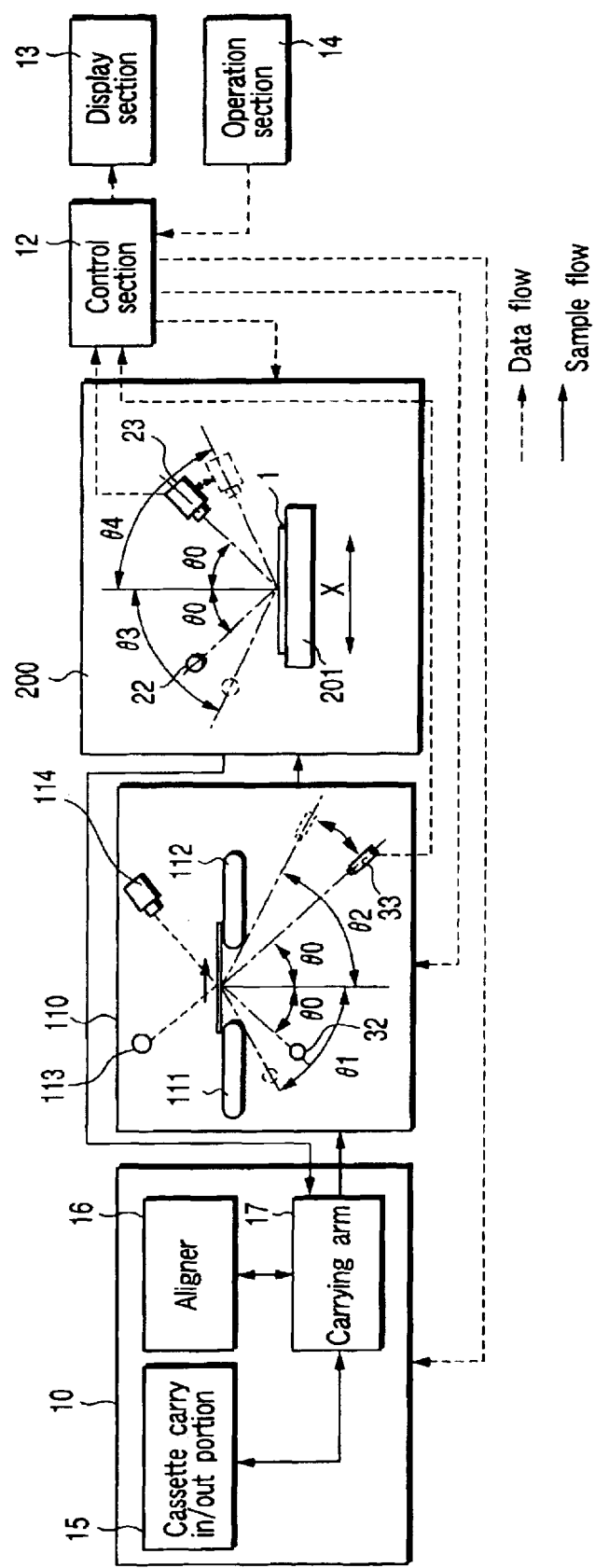
F I G. 13

DEFECT INSPECTION APPARATUS

CROSS-REFERENCE TO RELATED APPLICATIONS

This is a Continuation Application of PCT Application No. PCT/JP02/09762, filed Sep. 24, 2002, which was not published under PCT Article 21(2) in English.

This application is based upon and claims the benefit of priority from prior Japanese Patent Applications No. 2001-289963, filed Sep. 21, 2001; and No. 2002-080836, filed Mar. 22, 2002, the entire contents of both of which are incorporated herein by reference.

BACKGROUND OF THE INVENTION

1. Field of the Invention

The present invention relates to a defect inspection apparatus which applies illumination light to a sample such as a semiconductor wafer or a glass substrate of a flat display (FPD), and picks up an image of the light from the sample at this moment to perform defect inspection of the sample from image data thereof.

2. Description of the Related Art

Generally, in the middle of a manufacturing process of, for example, a semiconductor wafer or a glass substrate of a flat display, such as a manufacturing process having a photolithography process, there is a formation in which a patterned resist is provided on a substrate made of a silicon or glass plate via a film forming layer. However, in the photolithography process, if the resist applied to a substrate surface has an uneven film or dust sticking thereto, the uneven film or dust causes such defects as an irregular line width of the pattern or pin holes in the pattern after etching.

Under these circumstances, in the manufacturing process of the substrate before etching, all substrates are usually subjected to an inspection for finding the presence of the above defects. A method adopted to the total inspection often includes visual observation of all the substrates by operators. However, a difference of judgment of the operators dependent on experience and considerable effects of the dust made by the operators themselves in a clean room have led to a method in which the operators and the substrates are separated as far as possible to conduct observation, or a method which provides an apparatus with a judging function.

FIG. 16 is a diagram showing a configuration of a conventional defect inspection apparatus described in Jpn. Pat. Appln. KOKAI Publication No. 9-61365. An illumination section 2 and an image pickup section 3 are provided above a sample 1. The illumination section 2 applies illumination light to the sample 1 at an incidence angle $\theta_0$, and a collimator lens 4 is disposed in its light path and forms the illumination light from the illumination section 2 into a parallel light flux.

The image pickup section 3 is provided at a position opposite to the illumination section 2 with reference to a normal line n, and is disposed at an angle $\theta_0$ to the sample 1. The image pickup section 3 has a line sensor camera 5 and an image formation lens 6. A collimator lens 7 is disposed between the image pickup section 3 and the sample 1.

With such a configuration, a light flux, which is output from the illumination section 2 and diffused, is formed into the parallel light flux by the collimator lens 4 and gives line illumination to the sample 1. The light reflected on a surface of the sample 1 is incident upon the image formation lens 6 through the collimator lens 7, and is formed as an image of the surface of the sample 1 on an image pickup surface of the line sensor camera 5. Image data obtained by the image pickup with the line sensor camera 5 is then subjected to image processing, so as to perform the defect inspection of the surface of the sample 1.

In the manufacturing process having the photolithography process described above, when the resist is applied to the surface of the sample 1, the applied resist goes around to a rear surface of the sample 1 to, for instance, cause peripheral portions of the rear surface to bulge. However, under a current situation, even when the peripheral portions of the rear surface of the sample 1 bulge, or the rear surface of the sample 1 has flaws or dust sticking thereto, it is difficult to take measures for these problems because a technique described in the above-mentioned publication does not provide means to detect the rear surface of the sample.

BRIEF SUMMARY OF THE INVENTION

An object of the present invention is to provide a defect inspection apparatus capable of performing the defect inspection of the sample rear surface in addition to the defect inspection of the sample front surface.

The present invention provides a defect inspection apparatus comprising: an inspection section which inspects a front surface and a rear surface of a sample; a control section which processes image data on the front surface and rear surface of the sample obtained by the inspection section; moving section provided in the inspection section and capable of reciprocating the sample; illumination section which illuminates the front surface and rear surface of the sample moved by the moving section; and image pickup section which picks up images of the front surface and rear surface of the sample illuminated by the illumination section, wherein at least one of an incidence angle of the illumination section on the sample and an image pickup angle of the image pickup section to the sample is changeable.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a diagram showing a configuration of a defect inspection apparatus according to a first embodiment of the present invention;

FIG. 2A and FIG. 2B are diagrams showing a configuration of a holding member according to the first embodiment of the present invention;

FIG. 3A and FIG. 3B are diagrams showing the configuration of the holding member according to the first embodiment of the present invention;

FIG. 12 is a diagram showing the configuration of the defect inspection apparatus according to a fifth embodiment of the present invention;

FIG. 13 is a diagram showing the configuration of the defect inspection apparatus according to a modification of the fifth embodiment of the present invention;

DETAILED DESCRIPTION OF THE INVENTION

Figure 4:
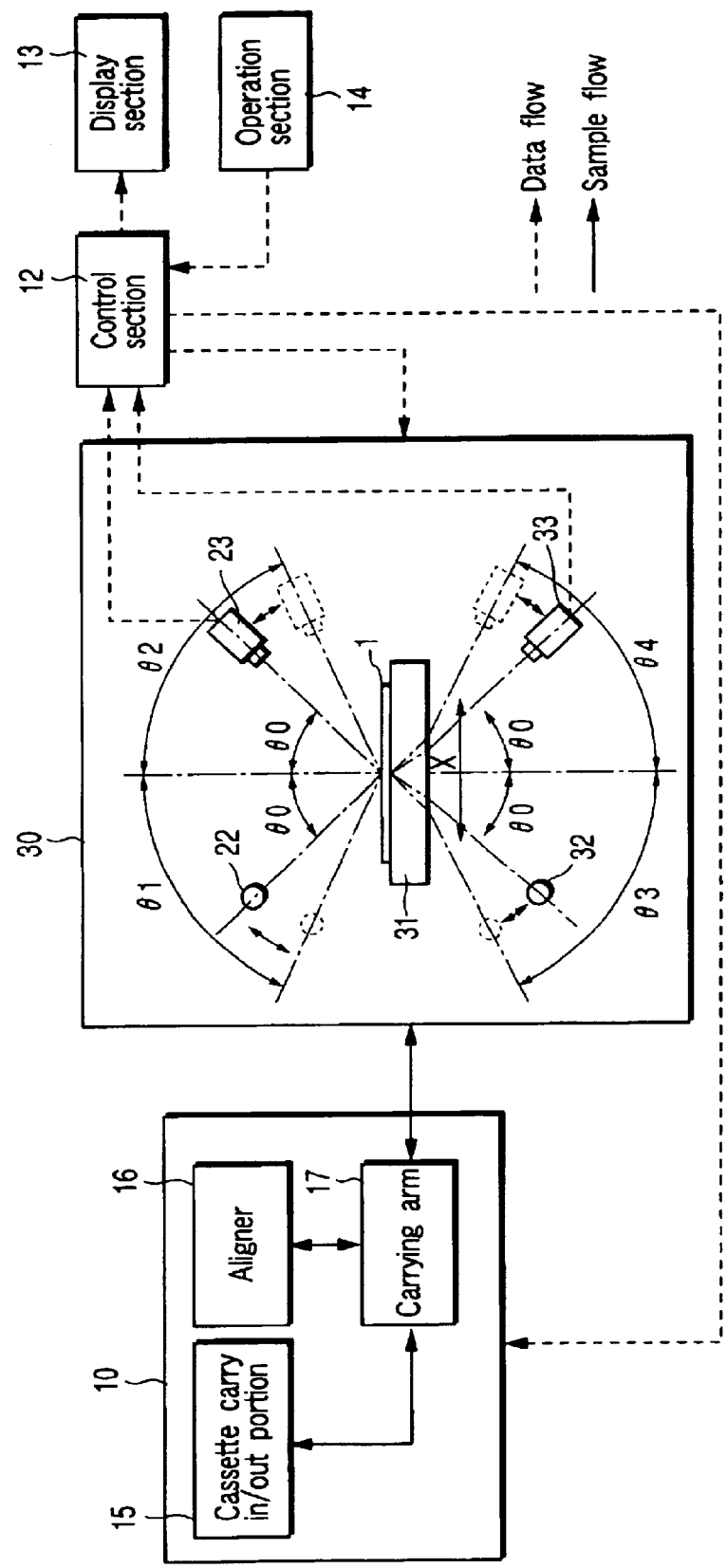
FIG. 4 is a diagram showing the configuration of the defect inspection apparatus according to a second embodiment of the present invention.

Embodiments of the present invention will hereinafter be described with reference to the drawings.

FIG. 1 is a diagram showing a configuration of a defect inspection apparatus according to a first embodiment of the present invention. In FIG. 1, arrows with broken lines indicate flow of data, and arrows with full lines indicate flow of a sample 1.

This defect inspection apparatus performs a defect inspection of the sample 1 including, for example, a semiconductor wafer or a glass substrate of a flat display. This defect inspection apparatus is generally comprised of a carrying section 10, an inspection section 11 performing the defect inspection of front and rear surfaces of the sample 1, a control section 12 which controls overall operation of the defect inspection, a display section 13 including, for example, a liquid crystal display with a touch sensor for displaying defect inspection results and the like, and an operation section 14 including, for example, a key board and a track ball for operating and inputting instructions and the like for the operation of the defect inspection.

The carrying section 10 carries the sample 1 to the inspection section 11, and is comprised of a cassette carry in/out portion 15, an aligner 16 and a carrying arm 17. The cassette carry in/out portion 15 has a function for a person (operator) or a robot to carry in and out the cassette containing a plurality of (e.g., twenty) samples 1 to the apparatus.

The aligner 16 has a function to align the sample 1 for higher accuracy of the defect inspection in the inspection section 11. The carrying arm 17 has a function to take out the samples 1 from the cassette carried into the cassette carry in/out portion 15 and carry them to the aligner 16 and the inspection section 11, respectively.

The inspection section 11 comprises a frame-shaped holding member 18 which holds a peripheral edge of the sample 1 so as to expose the front and rear surfaces of the sample 1. This holding member 18 inverts the sample 1 together with the holding member 18 by a rotation shaft 19 with an approximate center of thickness of the sample 1 as an axis, and sets one of the front and rear surfaces of the sample 1 into a attitude position for the defect inspection.

FIG. 2A and FIG. 2B are diagrams showing a configuration of the holding member 18. FIG. 2A is a diagram showing a state in which a semiconductor wafer which is the sample 1 is not held, and FIG. 2B is a diagram showing a state in which the semiconductor wafer (hereinafter simply referred to as a wafer) which is the sample 1 is held.

The holding member 18 is provided with a rigid frame 20 formed into an octagonal ring, and two sides opposite to each other of the frame 20 are provided with rotation shafts 19, 19, respectively. The rotation shafts 19, 19 are provided in such a manner that their shaft centers pass through a plane center (central position) of the sample 1 held by the frame 20 and through the thickness center of the sample 1. The rotation shafts 19, 19 invert the sample 1 held by the frame 20 frontward or rearward by rotating by 180 degrees.

The frame 20 is also provided with holding portions 21 on the inside of four of its sides, to hold the peripheral edge of the sample 1. These holding portions 21 stick fast to the peripheral edge on the rear surface of the sample 1, and have a function to stick fast to and hold the sample 1, for example, by vacuum sticking or an electrostatic chuck.

As shown in FIG. 1, the holding member 18 is capable of reciprocating movement in an X axis direction in order to obtain image data on the entire surface of the sample 1. Above the holding member 18, an inspection optical system linearly illuminates the sample surface in a Y axis direction that crosses the movement direction (X axis direction) of the holding member 18. A linear light source 22 and a line sensor camera 23 are provided. The linear light source 22 irradiates the sample 1 with linear parallel light. The line sensor camera 23 is provided at a position opposite to the linear light source 22 with reference to a normal line n, and picks up an image of the light reflected from the sample 1.

The linear light source 22 is set at a light irradiation angle $\theta_0$ to pick up an image of regular reflection (interference light) on the front or rear surface of the sample 1, and can turn within a range of a light irradiation angle $\theta_1$ to pick up an image other than the regular reflection on the front or rear surface of the sample 1. The line sensor camera 23 is set at an image pickup angle $\theta_0$ to pick up an image of the regular reflection on the front or rear surface of the sample 1, and can turn within a range of an image pickup angle $\theta_2$ to pick up an image other than the regular reflection on the front or rear surface of the sample 1.

The control section 12 has functions to, when inputting an operating instruction by the operator from the operation section 14, put out an instruction signal to each component of the apparatus, and receive an image signal output from the line sensor camera 23 to generate image data, and subject the image data to image processing to extract various kinds of defects in both the front and rear surfaces of the sample 1, and then display defect extraction results thereof on the display section 13.

Next, an operation of the defect inspection apparatus configured as above will be described. The following operation is performed under the control of the control section 12. When the cassette is set in the cassette carry in/out portion 15 by the operator or robot and the operator inputs an instruction for starting the operation from the operation section 14, the defect inspection of the sample 1 is started.

First, the carrying arm 17 vacuum-sticks to the sample 1 in the cassette to hold the sample 1, and carries the sample 1 to the aligner 16. The carrying arm 17 vacuum-sticks to the sample 1, which has been aligned by the aligner 16, to carry it to the inspection section 11, and sets it on the holding member 18 which waits in advance at a handover position in the inspection section 11.

Subsequently, the defect inspection of the sample 1 is started in the inspection section 11. During this inspection, the carrying arm 17 vacuum-sticks to the next sample 1 in the cassette to carry it to the aligner 16. The alignment of the sample 1 by the aligner 16 is finished before the defect inspection of the previous sample 1 in the inspection section 11 is finished.

When the sample 1 is set as shown in FIG. 2B, the holding member 18 of the inspection section 11 vacuum-sticks to the rear surface peripheral edge of the sample 1 by the respective holding portions 21 and holds it. The linear light source 22 is then set at a preset light irradiation angle $\theta_0$ to pick up an image of the regular reflection on the front surface of the sample 1. Along with this, the line sensor camera 23 is set at a preset image pickup angle $\theta_0$ to pick up an image of the regular reflection on the front surface of the sample 1.

When these settings are finished, the linear light source 22 outputs linear illumination light and applies this illumination light to the front surface of the sample 1 at the light irradiation angle $\theta_0$. Along with this, the holding member 18 starts moving toward an approach route in the X axis direction at a uniform velocity. Due to the movement of the holding member 18, the linear illumination light output from the linear light source 22 scans on the front surface of the sample 1 at a uniform velocity.

At the same time, the light reflected from the front surface of the sample 1 is taken into the line sensor camera 23. The line sensor camera 23 picks up an image of the linear regular reflection light from the front surface of the sample 1 formed on an image pickup surface, and outputs its image signal.

The control section 12 receives the image signals sequentially output from the line sensor camera 23, and generates one piece of regular reflection image data on the entire front surface of the sample 1. The control section 12 subjects the regular reflection image data to image processing to extract (detect) defects on the front surface of the sample 1, and displays defect extraction results thereof on the display section 13.

Next, the linear light source 22 is set at a light irradiation angle $\theta_1$, which is deflected from the light irradiation angle $\theta_0$ by a predetermined angle, to pick up an image other than the regular reflection (e.g., scattered light) on the front surface of the sample 1. In this case, the image pickup angle of the line sensor camera 23 may be set at an image pickup angle $\theta_2$ which is deflected from $\theta_0$ by a predetermined angle, instead of changing the light irradiation angle of the linear light source 22.

When these settings are finished, the holding member 18 moves toward the return route in the X axis direction at a uniform velocity and scans on the front surface of the sample 1 at a uniform velocity in accordance with the linear illumination light output from the linear light source 22.

The control section 12 receives the image signals output from the line sensor camera 23, and generates one piece of image data other than the regular reflection on the entire front surface of the sample 1. The control section 12 subjects the image data other than the regular reflection to image processing to extract (detect) defects on the surface of the sample 1, and displays defect extraction results thereof on the display section 13.

Next, the holding member 18 rotates by 180 degrees around the rotation shaft 19, and inverts the held sample 1 to set the rear surface to an inspection optical system side.

Similarly to the method to obtain the regular reflection image on the front surface of the sample 1 described above, the linear light source 22 and the line sensor camera 23 are set at the predetermined angle $\theta_0$ to obtain the regular reflection image on the rear surface of the sample 1.

When these settings are finished, the holding member 18 moves toward the approach route in the X axis direction at a uniform velocity and scans on the rear surface of the sample 1 at a uniform velocity in accordance with the linear illumination light output from the linear light source 22.

The line sensor camera 23 picks up an image of the linear light from the rear surface of the sample 1 formed on the image pickup surface, and outputs its image signal.

The control section 12 receives the image signal output from the line sensor camera 23, and generates one piece of image data on the entire rear surface of the sample 1. The control section 12 subjects the image data to image processing to extract (detect) defects on the rear surface of the sample 1, and displays defect extraction results thereof on the display section 13.

Similarly to the method to obtain the image other than the regular reflection on the front surface of the sample 1 described above, the linear light source 22 is reset at the light irradiation angle $\theta_1$.

When these settings are finished, the holding member 18 moves toward the return route in the X axis direction at a uniform velocity and scans on the rear surface of the sample 1 at a uniform velocity in accordance with the linear illumination light output from the linear light source 22.

The control section 12 receives the image signals output from the line sensor camera 23, and generates one piece of image data other than the regular reflection on the entire rear surface of the sample 1. The control section 12 subjects the image data to image processing to extract (detect) defects on the rear surface of the sample 1, and displays defect extraction results thereof on the display section 13.

When the image pickup in the return route on the rear surface of the sample 1 is thus finished, the holding member 18 again rotates by 180 degrees around the rotation shaft 19 to invert the sample 1, and sets the front surface of the sample 1 to the inspection optical system side similarly to when the inspection is started.

The holding member 18 then moves to a handover position with the carrying arm 17. Along with this, the linear light source 22 and the line sensor camera 23 are set at the angle $\theta_0$ to pick up a regular reflection image on the front surface of the next sample 1.

When the holding member 18 moves to the handover position with the carrying arm 17, the carrying arm 17 replaces the inspected sample 1 on the holding member 18 with the next sample 1 by one hand holding the sample 1 to be inspected next and by the other hand. The carrying arm 17 moves to the cassette carry in/out portion 15, and returns the inspected sample 1 held by the other hand to the cassette.

Subsequently, the above operation of the defect inspection is repeated, and all the samples 1 requiring the defect inspection are inspected.

In this way, in the first embodiment described above, the inspection section 11, which applies the illumination light to the sample 1 and picks up an image of the light reflected from the sample 1 to perform the defect inspection of the sample 1 from the image data, is provided with the holding member 18 which inverts the sample 1 around the rotation shaft 19 and sets one of the front and rear surfaces of the sample 1 to the attitude position for the defect inspection.

This allows the double side defect inspection of the front and rear surfaces of the sample 1. When the resist is applied to the front surface of the sample 1 in a manufacturing process having a photolithography process, the applied resist goes around to the rear surface of the sample 1 to, for instance, cause peripheral portions of the rear surface to bulge, but it is possible to detect such a bulge in the peripheral portions of the rear surface of the sample 1, flaws on the rear surface of the sample 1 and dust sticking thereto.

In this way, the holding member 18 inverts the sample 1, so that one inspection optical system including the linear light source 22 and the line sensor camera 23 may be provided, thus requiring no large space for its installation.

Furthermore, the rotatable light irradiation angle or image pickup angle of the linear light source 22 or the line sensor camera 23 enables the defect detection for the regular reflection image and the image other than the regular reflection on the front and rear surfaces of the sample 1 in different defect inspection methods. By changing the light irradiation angle in this way, a difference is made in how the state of the front and rear surfaces of the sample 1 looks, and the defect which could not be observed with one light irradiation angle can be observed with the other light irradiation angle. Therefore, by performing the defect inspection from two pieces of image data in different inspection methods, the defects are less overlooked to thereby enhance the accuracy of the defect inspection of the front and rear surfaces of the sample 1.

For example, the regular reflection image and the image other than the regular reflection can be synthesized to perform the defect inspection from the synthesized image data, or the defect inspection results by the regular reflection image and the defect inspection results by the image other than the regular reflection can be added to obtain results of the defect inspection.

In the first embodiment described above, a holding member 24 shown in FIG. 3A and FIG. 3B can be used instead of the holding member 18. FIG. 3A is an upper view, and FIG. 3B is a side view. This holding member 24 is comprised of holding portions 25 and 26 for pinching the sample 1 from its end (edge of the sample 1) sides opposite to each other, and rotation shafts 27 provided for the holding portions 25 and 26. As shown in FIG. 3A, the holding portions 25 and 26 have arch-shaped portions (ends) contacting the sample 1 so that they correspond to a circular outer shape of the sample 1, and as shown in FIG. 3B, V-shaped grooves 28 are formed in the arch-shaped ends. The holding portions 25 and 26 are provided movably in the Y axis direction, and hold the sample 1 by pinching the edge of the sample 1 in the grooves 28, 28.

Since the edge of the sample 1 is held by use of such a holding member 24, part of the rear surface of the sample 1 is not covered with the respective holding portions 21 as with the holding member 18 shown in FIG. 2A and FIG. 2B which vacuum-sticks to and holds the sample 1, and the grooves for vacuum formation and a sticking pad for sticking and holding are not formed in the holding portions 25 and 26, thereby enabling the simplification of the configuration.

Furthermore, the position of the holding member 24 can be accurately set to always provide a regular position and to provide the alignment by the aligner 16 only in the rotation direction for positioning a notch, thereby making it possible to increase an inspection rate and reduce costs.

FIG. 4 is a diagram showing the configuration of the defect inspection apparatus according to a second embodiment of the present invention. In FIG. 4, like numerals are given to like parts of FIG. 1 and are not described.

An inspection section 30 is provided with a holding member 31 formed of a light-transmitting material such as a glass material or transparent ceramic material. This holding member 31 comprises means for holding the entire surface or peripheral portion of the sample 1. The holding member 31 is capable of reciprocating movement in an X axis direction while holding the sample 1 as above. Above the holding member 31 (the front surface side of the sample 1), the linear light source 22 and the line sensor camera 23 are provided. Under the holding member 31 (the rear surface side of the sample 1), a linear light source 32 and a line sensor camera 33 are provided.

The linear light source 32 is set at the light irradiation angle $\theta_0$ to obtain a regular reflection image on the rear surface of the sample 1, and can turn within a range of a light irradiation angle $\theta_3$ to acquire an image other than the regular reflection on the rear surface of the sample 1. The line sensor camera 33 is set at the image pickup angle $\theta_0$ to acquire an image of the regular reflection on the rear surface of the sample 1, and can turn within a range of an image pickup angle $\theta_4$ to acquire an image other than the regular reflection on the rear surface of the sample 1.

Next, an operation of the defect inspection apparatus configured as above will be described. In this apparatus, the operation in the carrying section 10 is the same as that in the first embodiment and is thus not described, and the operation in the inspection section 30 will be described. The following operation is performed under the control of the control section 12.

When the sample 1 is set in the holding member 31 of the inspection section 30, it holds the rear surface peripheral edge of the sample 1 as the holding member 18 does in the first embodiment. The linear light sources 22, 32 on the front and rear sides are set at the light irradiation angle $\theta_0$ to pick up an image of the regular reflection on the front surface of the sample 1. Along with this, the line sensor cameras 23, 33 are set at the image pickup angle $\theta_0$ to pick up a regular reflection image on the front surface of the sample 1.

When these settings are finished, the linear light source 22 outputs linear illumination light on the front surface side of the sample 1 and applies this illumination light to the front surface of the sample 1 at the light irradiation angle $\theta_0$. Along with this, the holding member 31 starts moving toward the approach route in the X axis direction at a uniform velocity. Due to the movement of the holding member 31, the linear illumination light output from the linear light source 22 scans on the front surface of the sample 1 at a uniform velocity.

The light reflected from the front surface of the sample 1 is then taken into the line sensor camera 23. The line sensor camera 23 picks up an image of the linear regular reflection light from the front surface of the sample 1 formed on the image pickup surface, and outputs its image signal.

At the same time, the linear light source 32 outputs linear illumination light on the rear surface side of the sample 1 and applies this linear illumination light to the rear surface of the sample 1 at the light irradiation angle $\theta_0$. The illumination light is then incident into the holding member 31 of the light-transmitting material, and is refracted to be applied to the rear surface of the sample 1. The light reflected from the rear surface of the sample 1 then transmits through the holding member 31 and is refracted to emerge from the rear surface of the holding member 31.

The holding member 31 has started moving toward the approach route in the X axis direction at a uniform velocity as described above, so that, due to the movement of the holding member 31, the linear illumination light output from the linear light source 32 scans on the rear surface of the sample 1 at a uniform velocity.

The light reflected from the rear surface of the sample 1 is then taken into the line sensor camera 33. The line sensor camera 33 picks up an image of the linear regular reflection light from the rear surface of the sample 1 formed on the image pickup surface, and outputs its image signal.

The control section 12 receives the image signals output from the line sensor cameras 23, 33, and generates two pieces of regular reflection image data on the entire front and rear surfaces of the sample 1. The control section 12 subjects the regular reflection image data to image processing to extract (detect) defects on the front and rear surfaces of the sample 1, and displays defect extraction results thereof on the display section 13.

Next, the linear light source 22 on the front surface side of the sample 1 is set at the light irradiation angle $\theta_1$ to pick up an image other than the regular reflection on the front surface of the sample 1. Along with this, the linear light source 32 on the rear surface side of the sample 1 is set at another light irradiation angle $\theta_3$ to pick up an image other than the regular reflection on the rear surface of the sample 1.

When these settings are finished, the linear light sources 22, 32 output linear illumination lights on the front and rear surfaces sides of the sample 1 and apply the illumination lights to the front and rear surfaces of the sample 1 at the light irradiation angle $\theta_1$. Along with this, the holding member 31 starts moving toward the approach route in the X axis direction at a uniform velocity, so that the linear illumination lights output from the linear light sources 22, 23 scan on the front and rear surfaces of the sample 1 at a uniform velocity. The line sensor cameras 23, 33 then pick up images of the linear light from the front surface of the sample 1 formed on the image pickup surface, and output their image signals.

The control section 12 receives the image signals output from the line sensor cameras 23, 33, and generates two pieces of image data other than the regular reflection on the entire front and rear surfaces of the sample 1 when the linear illumination lights have finished scanning on the entire front and rear surfaces of the sample 1. The control section 12 subjects the image data other than the regular reflection to image processing to extract (detect) defects on the front and rear surfaces of the sample 1, and displays defect extraction results thereof on the display section 13.

When simultaneous image pickups on the front and rear surfaces of the sample 1 are finished as described above, the holding member 31 moves to the handover position with the carrying arm 17.

In this way, in the second embodiment described above, the inspection section 30 is provided with the holding member 31 formed of the light-transmitting material such as a glass material, and the inspection optical systems for the front and rear surfaces are respectively provided on both surfaces sides of the holding member 31. This allows the simultaneous defect inspection on the front and rear surfaces of the sample 1 with only one reciprocating movement of the holding member 31, which can reduce tact time of the double side inspection.

Furthermore, as in the first embodiment described above, when the resist is applied to the front surface of the sample 1 in the manufacturing process having the photolithography process, the applied resist goes around to the rear surface of the sample 1 to, for instance, cause the peripheral portions of the rear surface to bulge, but it is possible to detect such a bulge in the peripheral portions of the rear surface of the sample 1, flaws of the rear surface of the sample 1 and dust sticking thereto.

Still further, as in the first embodiment, different defect inspection methods are utilized to perform the defect detection with the regular reflection image and the image other than the regular reflection on the front and rear surfaces of the sample 1, thereby making it possible to enhance the accuracy of the defect inspection of the front and rear surfaces of the sample 1.

In addition, in the abovementioned second embodiment, the holding member 31 is formed of a transparent material and holds the entire surface of the sample 1, so that levelness of the sample 1 is improved and inspection accuracy can be enhanced.

Figure 5:
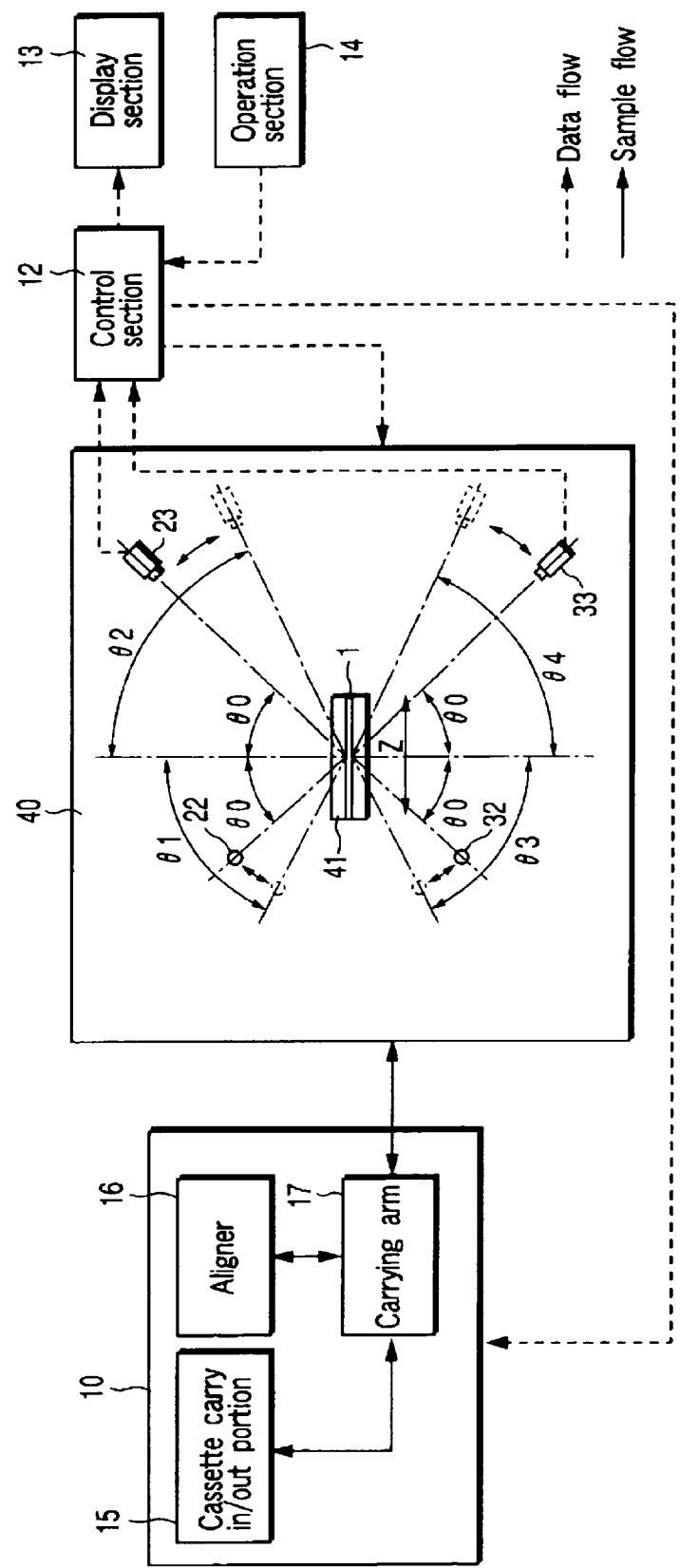
FIG. 5 is a diagram showing the configuration of the defect inspection apparatus according to a third embodiment of the present invention.

FIG. 5 is a diagram showing the configuration of the defect inspection apparatus according to a third embodiment of the present invention. In FIG. 5, like numerals are given to like parts of FIG. 1 and FIG. 4.

An inspection section 40 is provided with a holding member 41 which stands the sample 1 and holds the edge of the sample 1. This holding member 41 has the same shape and function as, for example, that of the holding member 24 shown in FIG. 3A and FIG. 3B described above. The holding member 41 is capable of, while standing the sample 1, reciprocating movement in a Z axis direction (upward and downward).

Therefore, the linear light source 22 and the line sensor camera 23 are provided on one surface side of the standing holding member 41 (the front surface side of the sample 1). The linear light source 32 and the line sensor camera 33 are provided on the other surface side of the holding member 41 (the rear surface side of the sample 1). The present third embodiment is different from the second embodiment shown in FIG. 4 only in that the inspection section 40 is stood, and is the same regarding the basic operation of the defect inspection apparatus, so that the operation will not be described.

In this third embodiment, the holding member 41 which stands the sample 1 and holds the edge of the sample 1 is provided in addition to the effects of the second embodiment described above, and therefore, the sample 1 is not distorted in the direction of gravity because of its weight, and it is possible to effectively perform the defect inspection of the large-sized sample 1, for example, a glass substrate of a large-sized liquid crystal display.

Figure 6A:
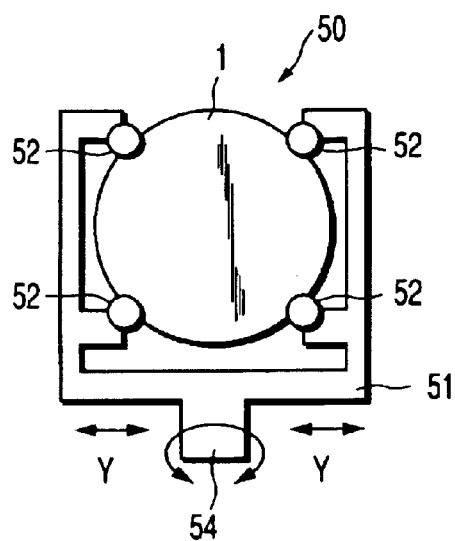
FIG. 6A, FIG. 6B and FIG. 7 are diagrams showing the configuration of the holding member according to the first to third embodiments of the present invention.
Figure 6B:
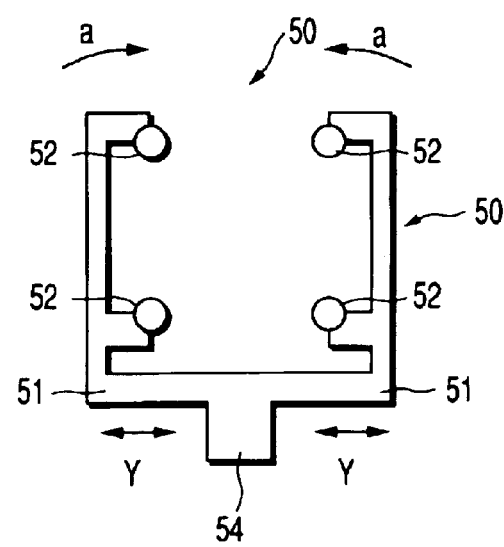
Figure 7:
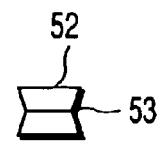

In addition, a holding member 50 shown in FIG. 6A, FIG. 6B may be used for the holding member of the sample 1 in the first to third embodiments described above. FIG. 6A is a diagram showing a state in which the sample 1 is held, and FIG. 6B is a diagram showing a state in which the sample 1 is not held. This holding member 50 has a frame 51 formed into a U shape, and is provided with pegs 52, at at least three positions, for example, four positions of the frame 51, for holding the sample 1. V-shaped grooves 53 are formed in these pegs 52, as shown in a sectional view of FIG. 7. In addition, to invert this holding member 50, the frame 51 may be provided with a rotation shaft 54. Further, if the frame 51 is provided with a biasing force in a direction of an arrow a toward an opening, it can facilitate the attachment of the sample 1.

Figure 8:
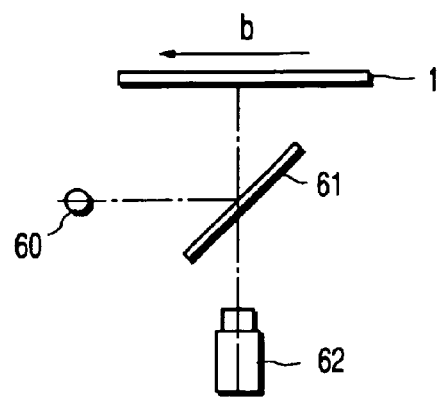
FIG. 8, FIG. 9 and FIG. 10 are diagrams showing a configuration of an inspection optical system according to the first to third embodiments of the present invention.
Figure 9:
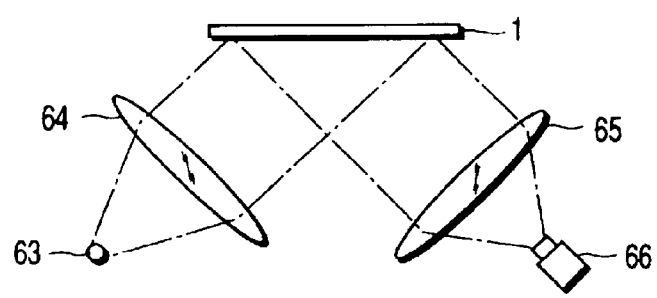
Figure 10:
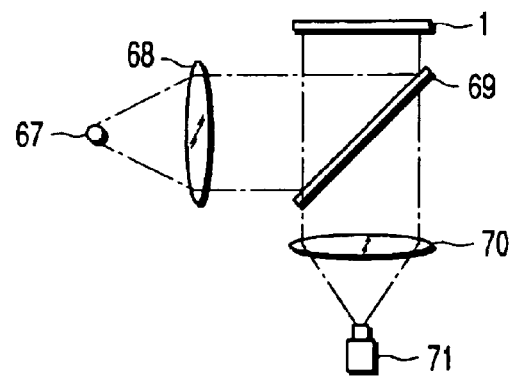

Furthermore, inspection optical systems having configurations shown in FIG. 8 to FIG. 10 may be used for the inspection optical systems in the first to third embodiments described above. The inspection optical system shown in FIG. 8 is comprised of a linear light source 60 which applies the line illumination light to the surface of the sample 1, a beam splitter (half mirror) 61 which reflects the line illumination light output from the linear light source 60 to irradiate the surface of the sample 1 therewith, and which transmits the light reflected from the surface of the sample 1, and a line sensor camera (image pickup means) 62 which picks up an image of the light that has transmitted through the beam splitter (half mirror) 61 and has been reflected from the surface of the sample 1.

In order to obtain image data on the surface of the sample 1 with this inspection optical system, the sample 1 is moved, for example, in a direction of an arrow b, and the line illumination light output from the linear light source 60 at this moment is applied to the surface of the sample 1, and then the line sensor camera 62 picks up an image of the reflected light thereof. With this inspection optical system, the linear light source 60 and the line sensor camera 62 allow for compact integration into one unit.

The inspection optical system shown in FIG. 9 is comprised of a light source 63 which outputs the illumination light, a first lens 64 which forms the illumination light from the light source 63 into a parallel light to apply it collectively to the entire surface of the sample 1, a second lens 65 which forms the light from the entire surface of the sample 1 into an image, and an image pickup means 66 which picks up the image of the light formed by the second lens 65. With such an inspection optical system, it is possible to collectively obtain the image data on the entire surface of the sample 1 without moving the sample 1.

The inspection optical system shown in FIG. 10 is comprised of a light source 67 which outputs the illumination light, a first lens 68 which forms the illumination light output from the light source 67 into a parallel light, a beam splitter (half mirror) 69 which reflects the linear illumination light from the first lens 68 to irradiate the surface of the sample 1 therewith, and which transmits the light reflected from the rear surface of the sample 1, a second lens 70 which forms into an image the light transmitted through the beam splitter 69 from the entire surface of the sample 1, and an image pickup device 71 which picks up the image of the light formed by the second lens 70. With such an inspection optical system, it is also possible to collectively obtain the image data on the entire surface of the sample 1 without moving the sample 1.

Furthermore, the "regular reflection image" described in the above first to third embodiments may be an interference image picked up by use of an interference filter. The interference image can be obtained by picking up images of, through the interference filter, a light reflected from the front surface of the sample 1 and a light reflected from a lower layer when the illumination light is applied to the sample 1. Further, the "image other than the regular reflection" described in the above first to third embodiments may be a diffraction image or a scattered light observation image.

Figure 11:
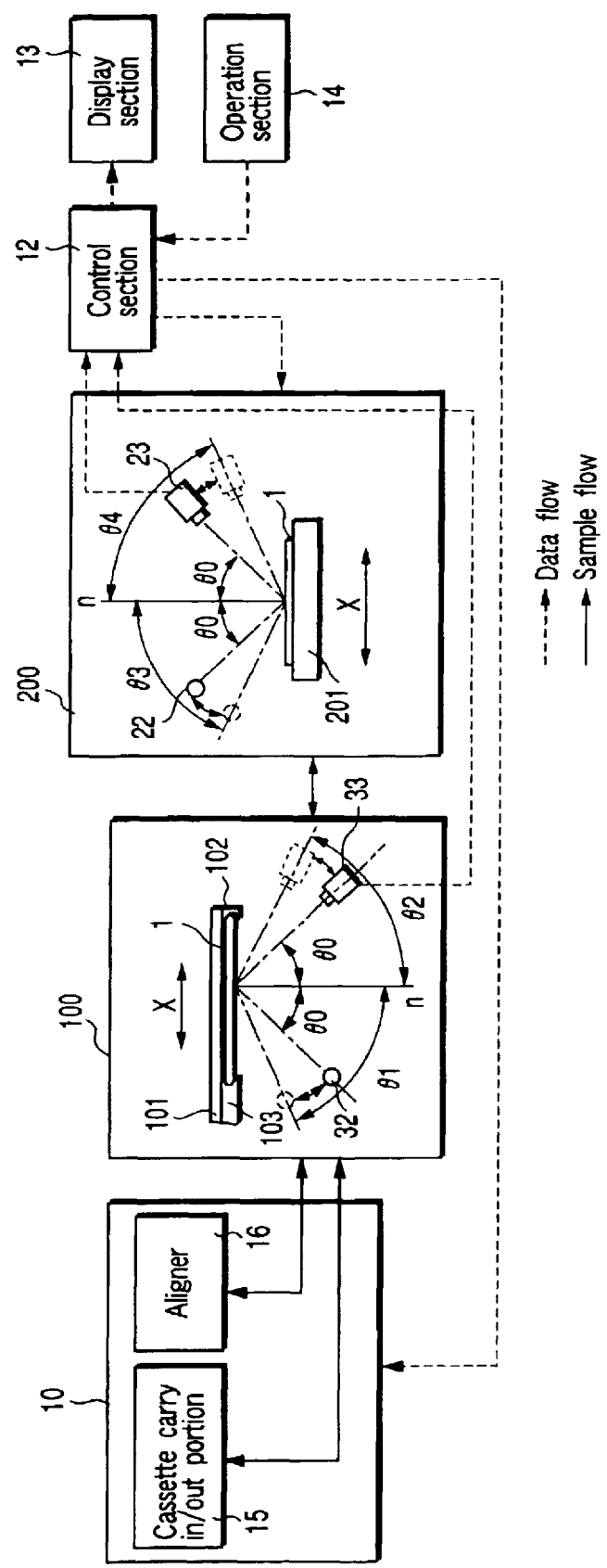
FIG. 11 is a diagram showing the configuration of the defect inspection apparatus according to a fourth embodiment of the present invention.

FIG. 11 is a diagram showing the configuration of the defect inspection apparatus according to a fourth embodiment of the present invention. In FIG. 11, like numerals are given to like parts of FIG. 1 and FIG. 5 and are not described. In this fourth embodiment, a rear surface inspection section 100 of the present embodiment is disposed in a carrying path of the carrying arm 17 of the first embodiment shown in FIG. 1.

The rear surface inspection section 100 is provided in the carrying path of the sample 1 between the carrying section 10 and a front surface inspection section 200, and has a function to apply the illumination light to the rear surface of the sample 1, and pick up an image of the light from the rear surface of the sample 1 to obtain its image data.

The rear surface inspection section 100 is provided with a carrying arm 101 as the holding member which holds the sample 1 leaving at least its rear surface open. The carrying arm 101 has an downward locking portion 102 formed at its end, and is provided, on its lower side, with a movable holding portion 103 slidably in a direction of a main body of the carrying arm 101. Thereby, the carrying arm 101 holds tightly, with the locking portion 102 and the movable holding portion 103, the sample 1 handed over by the aligner 16 so that its rear surface faces downward, and in this state, carries the sample 1 to the front surface inspection section 200 in a X direction at a certain carrying speed (uniform velocity).

Furthermore, under the carrying path of the carrying arm 101, the rear surface inspection section 100 is provided with the linear light source 32 which applies a linear parallel light to the sample 1, and the line sensor camera 33. The linear light source 32 is set at the light irradiation angle $\theta_0$ to obtain a regular reflection image on the rear surface of the sample 1, and can turn within the range of the light irradiation angle $\theta_1$ to pick up an image other than the regular reflection. The line sensor camera 33 is set at the image pickup angle $\theta_0$ to acquire an image of the regular reflection (interference light) on the rear surface of the sample 1, and can turn within the range of the image pickup angle $\theta_2$ to pick up an image other than the regular reflection (scattered light or diffracted light).

The rear surface inspection section 100 switches between the image pickup angles $\theta_0$ and $\theta_2$ respectively when the carrying arm 101 holds the sample 1 and carries it to the front surface inspection section 200 and when the carrying arm 101 holds the sample 1 and returns from the front surface inspection section 200 to the carrying section 10, thus picking up images of the rear surface of the sample 1 at the different angles so as to obtain two pieces of image data on, for example, the interference light and scattered light. In other words, by changing the light irradiation angle to the rear surface of the sample 1, a difference is made in how the state of the rear surface of the sample 1 looks, and the defect which could not be observed with one light irradiation angle can be observed with the other light irradiation angle.

The front surface inspection section 200 comprises a holding member (inspection stage) 201 which holds the sample 1. This holding member 201 is capable of reciprocating movement in the X axis direction to obtain the image data on the entire surface of the sample 1. Above the holding member 201, the linear light source 22 and the line sensor camera 23 are provided as the inspection optical system. The linear light source 22 applies a linear parallel light to the sample 1. The line sensor camera 23 is provided at a position opposite to the linear light source 22 with reference to the normal line n, and picks up an image of the light reflected from the sample 1.

The linear light source 22 is set at the light irradiation angle $\theta_0$ to pick up an image of the regular reflection on the front surface of the sample 1, and can turn within the range of the light irradiation angle $\theta_3$ to pick up an image other than the regular reflection on the front surface of the sample 1. The line sensor camera 23 is set at the image pickup angle $\theta_0$ to pick up an image of the regular reflection (interference light) on the front surface of the sample 1, and can turn within a range of an image pickup angle $\theta_4$ to pick up an image other than the regular reflection on the front surface of the sample 1.

In this fourth embodiment described above, the rear surface inspection section 100 is provided between the carrying section 10 and the front surface inspection section 200, and in this rear surface inspection section 100, an image of the rear surface of the sample 1 being carried at a certain carrying speed by the carrying arm 101 is picked up. This rear surface inspection section 100 enables the defect inspection of the rear surface of the sample 1 in addition to the defect inspection of the front surface of the sample 1 in the front surface inspection section 200. Moreover, this defect inspection of the rear surface of the sample 1 is performed by obtaining the image data while the sample 1 is being carried between the carrying section 10 and the front surface inspection section 200, thus requiring no time for the defect inspection of the rear surface of the sample 1 and allowing the tact time to be reduced.

Furthermore, as in each of the embodiments described above, when the resist is applied to the front surface of the sample 1 in the manufacturing process having the photolithography process, the applied resist goes around to the rear surface of the sample 1 to, for instance, bulge the peripheral portions of the rear surface, but it is possible to detect such a bulge in the peripheral portions of the rear surface of the sample 1, flaws on the rear surface of the sample 1 and dust sticking thereto.

Still further, different defect inspection methods are utilized to perform the defect inspection with the regular reflection image and the image other than the regular reflection on the front and rear surfaces of the sample 1, thereby making it possible to enhance the accuracy of the defect inspection for the front and rear surfaces of the sample 1.

In addition, the holding member 50 shown in FIG. 6A, FIG. 6B may be used for the carrying arm 101 in the fourth embodiment described above.

FIG. 12 is a diagram showing the configuration of the defect inspection apparatus according to a fifth embodiment of the present invention. In FIG. 12, like numerals are given to like parts of FIG. 1 and FIG. 11 and are not described. In this fifth embodiment, the carrying section 10 is the same as that in FIG. 1, and the front surface inspection section 200 is the same as that in FIG. 11. The difference from FIG. 11 is a rear surface inspection section 110.

The rear surface inspection section 110 is provided between the carrying section 10 and the front surface inspection section 200. The carrying arm 17 of the carrying section 10 receives the sample 1 aligned by the aligner 16, and vacuum-sticks to and holds the sample 1 so as to carry it to the rear surface inspection section 110. Further, the carrying arm 17 has a function to take out the samples 1 from the cassette carried in the cassette carry in/out portion 15, and a function to carry them to the cassette carry in/out portion 15, the aligner 16 and the rear surface inspection section 11, respectively.

The rear surface inspection section 110 comprises non-contact carrying conveyers 111, 112 such as two air cushions which carry the sample 1 at a certain carrying speed (uniform velocity) to hand it over to the front surface inspection section 200. The carrying conveyers 111, 112 take and carry the sample 1 to the front surface inspection section 200 at a certain carrying speed. The linear light source 32 and the line sensor camera 33 are disposed between the carrying conveyers 111 and 112, as in the rear surface inspection section 100 of FIG. 11.

The linear light source 32 applies the illumination light to the rear surface of the sample 1 through a clearance between the two carrying conveyers 111 and 112. As in the fourth embodiment, the linear light source 32 is set at the light irradiation angle $\theta_0$ to obtain the regular reflection image on the rear surface of the sample 1, and can turn within the range of the light irradiation angle $\theta_1$ to pick up an image other than the regular reflection. The line sensor camera 33 picks up an image of the rear surface of the sample 1 through the clearance between the two carrying conveyers 111 and 112. As in the fourth embodiment described above, this line sensor camera 33 is set at the image pickup angle $\theta_0$ to acquire an image of the regular reflection on the rear surface of the sample 1, and can turn within the range of the image pickup angle $\theta_2$ to pick up an image other than the regular reflection.

Next, an operation of the defect inspection apparatus configured as above will be described. The following operation is performed under the control of the control section 12.

First, the carrying arm 17 vacuum-sticks to the sample 1 in the cassette to hold the sample 1, and carries the sample 1 to the aligner 16. The carrying arm 17 holds the sample 1 after it is aligned by the aligner 16, and puts the sample 1 on the carrying conveyer 111 of the rear surface inspection section 110.

The carrying conveyers 111, 112 carry the sample 1 to the front surface inspection section 200 at a certain carrying speed directly or by putting the sample 1 on a carrying chuck table. The sample 1 then passes through the clearance between the two carrying conveyers 111 and 112 at a certain carrying speed. At this moment, the linear light source 32 is set at the light irradiation angle $\theta_0$ to obtain the regular reflection image on the rear surface of the sample 1. Along with this, the line sensor camera 33 is set at the image pickup angle $\theta_0$.

When these settings are finished, the linear light source 33 applies, at the light irradiation angle $\theta_0$, the illumination light to the rear surface of the sample 1 which passes through the clearance between the two carrying conveyers 111 and 112 at a certain carrying speed. Along with this, the line sensor camera 33 takes in the regular reflection light from the rear surface of the sample 1, and picks up an image of the linear light from the rear surface of the sample 1 formed on the image pickup surface, and outputs their image signals.

The control section 12 receives the image signals output from the line sensor camera 33, and generates one piece of regular reflection image data on the entire rear surface of the sample 1.

The sample 1 which has passed through the rear surface inspection section 110 is handed over to the holding member 201 which waits in advance at the handover position in the front surface inspection section 200. When the sample 1 is set on the holding member 201, the inspection in the front surface inspection section 200 is performed in the same way as in the fourth embodiment.

When the inspection in the front surface inspection section 200 is finished, the holding member 201 moves to the handover position with the carrying conveyer 112, and puts the sample 1 on the carrying conveyer 112. The sample 1 is carried to the carrying section 10 at a certain carrying speed by the carrying conveyers 111, 112. At this moment, the sample 1 passes through the clearance between the two carrying conveyers 111 and 112 at a certain carrying speed.

The linear light source 32 is then set at the light irradiation angle $\theta_1$, which is deflected from the light irradiation angle $\theta_0$ by a predetermined angle, to pick up an image other than the regular reflection (e.g., scattered light) on the rear surface of the sample 1. The linear light source 32 outputs a linear illumination light and applies this illumination light to the rear surface of the sample 1 at the light irradiation angle $\theta_1$. Along with this, the line sensor camera 33 takes in the scattered light from the rear surface of the sample 1, and picks up an image of the linear light from the rear surface of the sample 1 formed on the image pickup surface, and outputs its image signal.

The control section 12 receives the image signals output from the line sensor camera 33, and generates one piece of image data other than the regular reflection on the entire rear surface of the sample 1. The control section 12 subjects the image data other than the regular reflection to image processing to extract (detect) defects on the rear surface of the sample 1, and displays defect extraction results thereof on the display section 13.

In this fifth embodiment described above, the rear surface inspection section 110 is provided between the carrying section 10 and the front surface inspection section 200, and in this rear surface inspection section 110, an image of the rear surface of the sample 1 is picked up while the sample 1 is being carried by the two carrying conveyers 111 and 112 at a certain carrying speed. This off course provides the same effects as in the fourth embodiment described above, and the image of the rear surface of the sample 1 is picked up when the sample 1 passes through the clearance between the two carrying conveyers 111 and 112, thereby allowing the entire rear surface of the sample 1 to be inspected perfectly.

In addition, the fifth embodiment described above may be modified in the following manner. For example, a belt conveyor or a roller conveyor may be used, and the sample 1 may be carried in a non-contact manner by blowing air (compressed air) thereto from beneath or floating the sample 1 in the air by use of magnetism. Further, as means for carrying the sample 1, ultrasonic waves may be utilized to float and carry the sample 1.

Furthermore, one set of linear light source and line sensor camera is provided as image pickup means, but a plurality of sets each having a different light irradiation angle and image pickup angle may be provided. This makes it possible to obtain two pieces of image data in different defect inspection methods with movement in one direction during the rear surface inspection when the sample 1 is carried to the front surface inspection section 200, and during the front surface inspection in the front surface inspection section 200.

FIG. 13 is a diagram showing the configuration of the defect inspection apparatus according to a modification of the fifth embodiment of the present invention. In FIG. 13, like numerals are given to like parts of FIG. 12 of the fourth embodiment. In the fifth embodiment, a light source 113 for picking up an image of the front surface of the sample 1, and a line sensor camera 114 are disposed in the rear surface inspection section 110 of FIG. 12. This makes it possible to obtain image data on the front surface of the sample 1 which is carried by the two carrying conveyers 111 and 112 at a uniform velocity.

Figure 14:
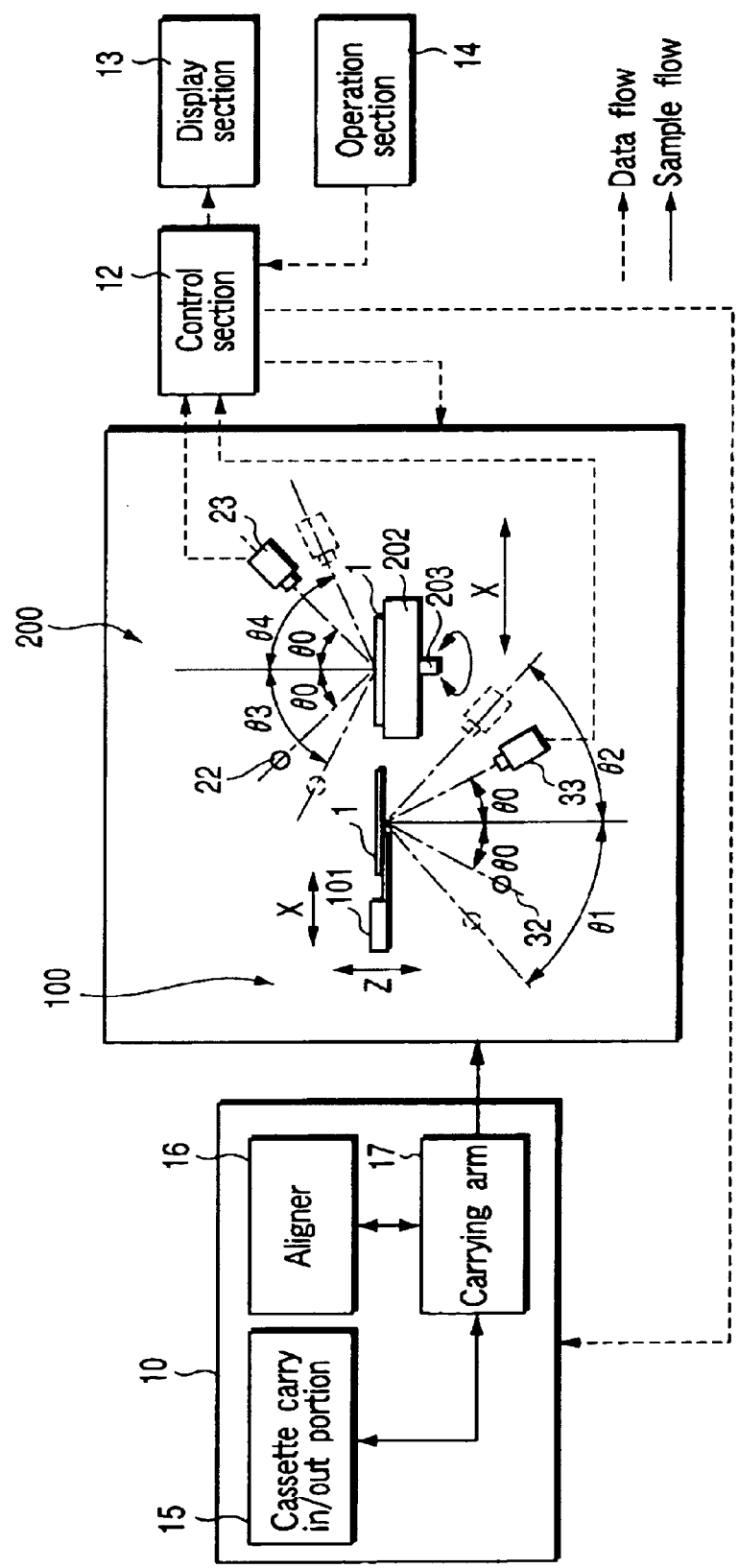
FIG. 14 is a diagram showing the configuration of the defect inspection apparatus according to a sixth embodiment of the present invention.

FIG. 14 is a diagram showing the configuration of the defect inspection apparatus according to a sixth embodiment of the present invention. In FIG. 14, like numerals are given to like parts of FIG. 11 of the fourth embodiment.

The carrying section 10 and the rear surface inspection section 100 have about the same configuration as in the fourth embodiment. A holding member 202 of the front surface inspection section 200 is coupled to a rotation shaft 203 and is capable of rotating by 360 degrees. The holding member 202 is preferably provided with a rotating stage which puts the sample (semiconductor wafer) 1 on a stage capable of uniaxial movement, and this rotating stage is rotated. This front surface inspection section 200 of the sixth embodiment has about the same configuration except that a rotating function is added to the holding member 201 of the fourth embodiment.

Next, an operation of the defect inspection apparatus configured as above will be described. The following operation is performed under the control of the control section 12. In addition, the carrying section 10 and the rear surface inspection section 100 are the same as in the fourth embodiment described above, so that an operation in the front surface inspection section 200 will be described here.

When the sample 1 is set onto the holding member 202 from the carrying arm 101, the linear light source 22 and the line sensor camera 23 are set at the angle $\theta_0$ to pick up an image of the regular reflection (interference) on the front surface of the sample 1, as in the fourth embodiment described above.

The control section 12 receives the image signals output from the line sensor camera 23, and generates one piece of regular reflection (interference) image data on the entire front surface of the sample 1. The control section 12 subjects the regular reflection image data to image processing to extract (detect) defects on the front surface of the sample 1, and displays defect extraction results thereof on the display section 13.

Next, the linear light source 22 is set at the light irradiation angle $\theta_3$, which is deflected from the light irradiation angle $\theta_0$ by a predetermined angle, to pick up an image other than the regular reflection (e.g., scattered light, diffracted light) on the front surface of the sample 1, as in the fourth embodiment described above.

The control section 12 receives the image signals output from the line sensor camera 23, and generates one piece of image data other than the regular reflection on the entire front surface of the sample 1. The control section 12 subjects the image data other than the regular reflection to image processing to extract (detect) defects on the front surface of the sample 1, and displays defect extraction results thereof on the display section 13.

The operation of the front surface inspection section 200 described above is the same as in the fourth embodiment, and the operation described below is different from that in the fourth embodiment. The holding member 202 rotates, while the sample 1 is being placed thereon, in a direction that allows the scattered light (or diffracted light) to be satisfactorily taken in or in a direction that allows the interference light to be satisfactorily taken in without being affected by the diffracted light from a base pattern, thereby turning the sample 1 toward an incidence direction of the linear light source 22.

Next, the holding member 202 again moves in the X direction, and the linear light source 22 is set at the light irradiation angle $\theta_0$ or $\theta_3$ in the same way as described above, and then the regular reflection image or the image other than the regular reflection on the front surface of the sample 1 is obtained with the line sensor camera 23.

In this way, in the sixth embodiment, the sample 1 on the holding member 202 can be turned into an optional direction toward the incidence direction of the linear light source 22 during the front surface defect inspection of the sample 1. This makes it possible to satisfactorily take in the regular reflection image or the image other than the regular reflection toward the direction of the pattern or defects. By changing the light irradiating direction and making difference in how the state of the front surface of the sample 1 looks in this way, the defect which could not be observed with the light irradiation angle in one direction can be observed, and reliability of the defect inspection can be enhanced.

In addition, in the fourth or sixth embodiment described above, a plurality of carrying arms are provided, and the sample 1 is placed on the holding member of the inspection section by any one of the carrying arms, and then while the front surface of the sample 1 is being inspected in the front surface inspection section 200, the next sample 1 is received by the other carrying arm and the rear surface of the sample 1 is inspected in the rear surface inspection section 100 and put on standby. It is thus possible to reduce the inspection time by providing a plurality of carrying arms.

Figure 15:
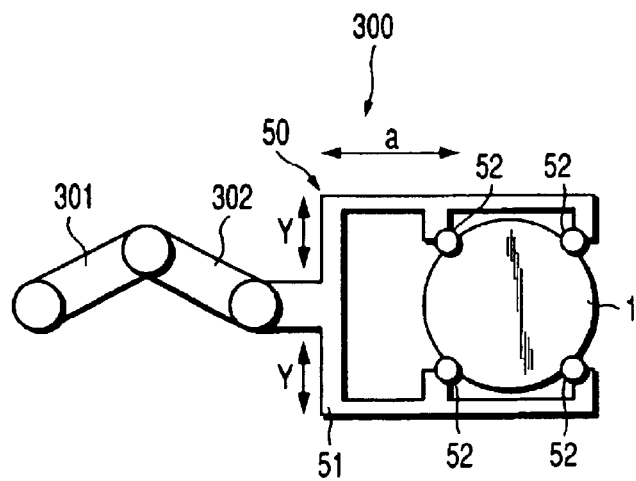
FIG. 15 is a diagram showing a configuration of a carrying arm according to the fourth to sixth embodiments of the present invention.
Figure 16:
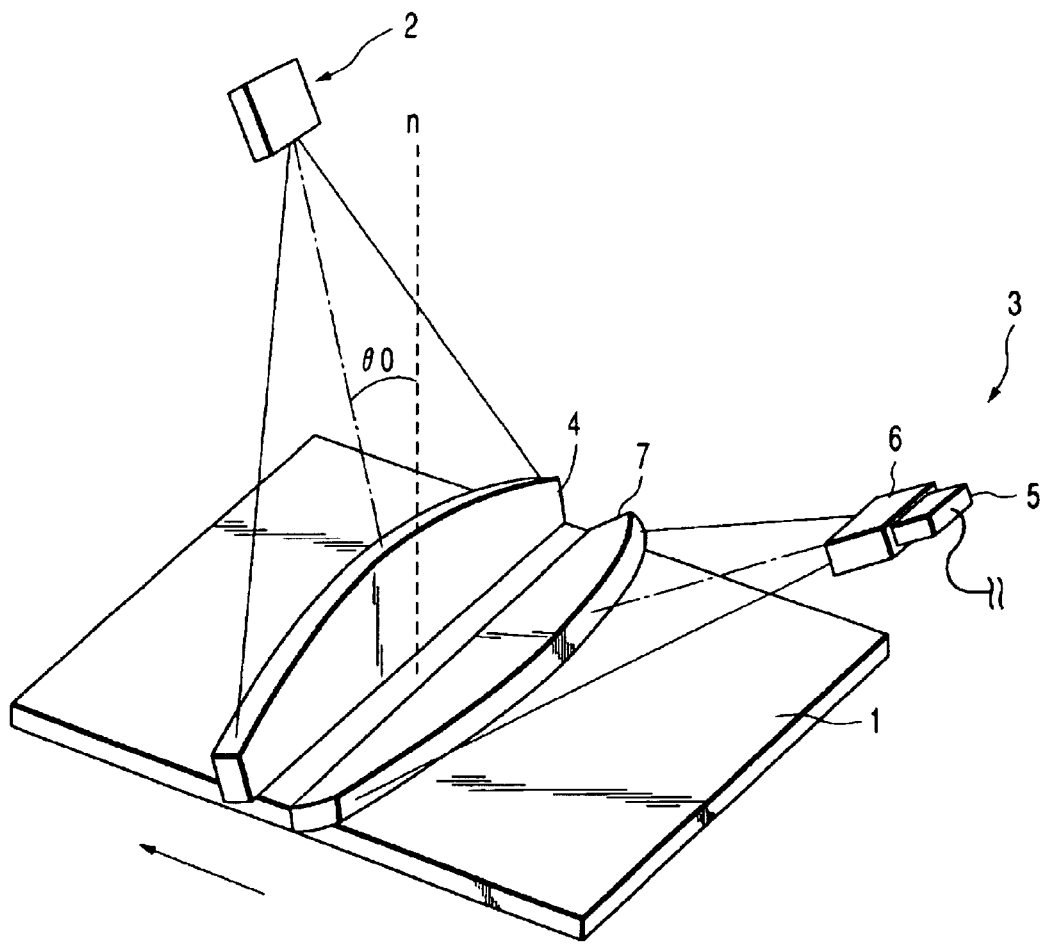
FIG. 16 is a diagram showing a configuration of a defect inspection apparatus according to a conventional example.

In addition, the carrying arm used in the fourth or sixth embodiment described above can be replaced with a carrying robot arm 300 shown in FIG. 15. In FIG. 15, like numerals are given to like parts of FIG. 6A and FIG. 6B. In this carrying robot arm 300, the holding member 50 shown in FIG. 6A for holding tightly an edge of the sample 1 is coupled to an end of arms 301, 302 having multiple joints, for example, three joints, and the holding member 50 can be directly moved in an arrow a direction by the operation of the arms 301, 302.

Furthermore, what is referred to as a double arm using the two carrying robot arms 300 can be used instead of the above carrying arm 101. If this double arm is used, the next sample 1 can be inspected in the rear surface inspection section 100 while the front surface of the sample 1 is being inspected by one of the carrying robot arms 300 in the front surface inspection section 200, thus allowing the inspection time to be reduced.

It should be noted that the present invention is not limited to the fourth to sixth embodiments described above, and can be variously modified at an implementation stage without departing from the spirit thereof.

For example, in the rear surface inspection sections 100 and 110, the holding member 18 having the configuration shown in FIG. 2A and FIG. 2B may be used for the holding member for holding the sample 1. As another holding member, the holding member 24 shown in FIG. 3A and FIG. 3B can be used. On the other hand, the inspection optical system having the configuration shown in FIG. 8 to FIG. 10 may be used for the inspection optical system on the rear surface of the sample 1 in the fourth to sixth embodiments described above.

The present invention is not limited to only the embodiments described above, and can be appropriately modified for implementation without departing from the spirit thereof.

According to the present invention, a defect inspection apparatus can be provided which is capable of performing the defect inspection of the sample rear surface in addition to the defect inspection of the sample front surface.

Furthermore, according to the present invention, it is possible to provide a defect inspection apparatus which enhances the accuracy of defect inspection results with a regular reflection image on the front and rear surfaces of the sample and a plurality of images other than the regular reflection in different defect inspection methods, and which deceases overlooks of defects by use of a synthesized image of the plurality of images in the different defect inspection methods to enhance the accuracy of the defect inspection of the rear surface of the sample.

Still further, according to the present invention, it is possible to provide a defect inspection apparatus which can simultaneously perform the defect inspection on the front surface and rear surface of the sample and which can reduce tact time of the double side inspection.

Further yet, according to the present invention, it is possible to provide a defect inspection apparatus which does not cause the sample to be distorted in a direction of gravity because of its weight by standing the sample, thereby being effective for the defect inspection of a large-sized sample.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A defect inspection apparatus comprising:
   an inspection section which inspects a front surface and a rear surface off a sample;
   a control section which processes image data of the front surface and the rear surface of the sample obtained by the inspection section;
   a front surface moving section provided in the inspection section which moves the sample for inspection of the front surface;
   a rear surface moving section provided in the inspection section which moves the sample for inspection of the rear surface; and
   a front surface illumination section and a rear surface illumination section which respectively illuminate the front surface and the rear surface for inspection;
   a front surface image pickup section and a rear surface image pickup section which respectively pick up an image of the illuminated front surface and an image of the illuminated rear surface;
   wherein at least one of: (i) respective incidence angles of the front surface illumination section and the rear surface illumination section on the sample, and (ii) respective image pickup angles of the front surface image pickup section and the rear surface image pickup section with respect to the sample, are changeable;
   wherein the rear surface illumination section and the rear surface image pickup section are arranged along moving path of the rear surface moving section to inspect the rear surface of the sample;
   wherein at least the rear surface illumination section comprises a linear light source which irradiates a linear parallel light beam to the rear surface of the sample at a predetermined incidence angle, and at least the rear surface image pickup section comprises a line sensor camera which picks up the image of the rear surface illuminated by the light beam from the linear light source; and
   wherein the sample is moved to and from the front surface moving section via at least the rear surface moving section, and the rear surface of the sample is inspected while the rear surface moving section moves the sample.

2. The apparatus according to claim 1, wherein the rear surface moving section moves the sample at constant velocity.

3. The apparatus according to claim 1, wherein the rear surface moving section comprises a carrying arm which holds the sample while exposing the rear surface of the sample.

4. The apparatus according to claim 1, wherein the rear surface moving section comprises a plurality of non-contact carrying conveyers which carry the sample, and wherein a clearance is provided in a carrying path of the carrying conveyors such that the image of the rear surface is picked up through the clearance.

5. The apparatus according to claim 1, further comprising a carrying section which carries the sample to the inspection section;

wherein the inspection section comprises: (i) a front surface inspecting section including the front surface moving section, the front surface illuminating section and the front surface image pickup section, for inspecting the front surface of the sample, and (ii) a rear surface inspection section including the rear surface moving section, the rear surface illuminating section and the rear surface image pickup section, for inspecting the rear surface of the sample; and wherein the rear surface inspection section is provided between the carrying section and the front surface inspection section.

6. The apparatus according to claim 1, wherein the incidence angle of the front surface illumination section and the image pickup angle of the front surface image pickup section are set as a first angle to pick up a regular reflection image of the front surface at a first image pickup time, and at least one of the incidence angle of the front surface illumination section and the image pickup angle of the front surface image pickup section is set as a second angle different from the first angle to pick up an image of the front surface other than the regular reflection image of the front surface at a second image pickup time; and wherein the incidence angle of the rear surface illumination section and the image pickup angle of the rear surface image pickup section are set as a first angle to pick up a regular reflection of the rear surface image at a first image pickup time, and at least one of the incidence angle of the rear surface illumination section and the image pickup angle o the rear surface image pickup section is set as a second angle different from the first angle to pick up an image of the rear surface image other than the regular reflection image of the rear surface image at a second image pickup time.

7. The apparatus according to claim 6, wherein the regular reflection images of the front surface and the rear surface are picked up when, the sample is moved in a first direction, and the images of the front surface and the rear surface other than the regular reflection images are picked up when the sample is moved in a direction opposite to the first direction.

* * * * *